United States Patent [19]

Kairis et al.

[11] Patent Number: 4,694,840
[45] Date of Patent: Sep. 22, 1987

[54] ELECTRO-THERAPEUTIC DEVICE

[75] Inventors: Alexandre Kairis; Ronnie H. Colsen, both of Tokyo, Japan

[73] Assignee: 501 Waco Trading Corporation, Tokyo, Japan

[21] Appl. No.: 825,919

[22] Filed: Feb. 4, 1986

Related U.S. Application Data

[63] Continuation-in-part of Ser. No. 601,167, Apr. 17, 1984, abandoned.

[30] Foreign Application Priority Data

Oct. 25, 1983 [JP] Japan ............................ 58-164090[U]
Nov. 16, 1983 [JP] Japan ............................ 58-176085[U]

[51] Int. Cl.$^4$ ............................................. A61B 5/05
[52] U.S. Cl. ................................. 128/735; 128/419 R; 128/907
[58] Field of Search ............... 128/734, 735, 800, 801, 128/303.13, 907, 419 R, 419 PG

[56] References Cited

U.S. PATENT DOCUMENTS 3,207,151  9/1965  Takagi ........................... 128/419 R
3,894,532  7/1975  Morey ................................ 128/735
4,112,923  9/1978  Tomecek ............................ 128/735
4,494,554  9/1985  Van Dyke et al. ................. 128/734

FOREIGN PATENT DOCUMENTS 2418646  2/1979  France ................................ 128/735
2430225  7/1980  France ................................ 128/907
1126634  9/1968  United Kingdom ................. 128/735

Primary Examiner—Edward M. Coven
Attorney, Agent, or Firm—Morgan & Finnegan

[57] ABSTRACT

A probing and stimulating device (10) for a sensitive point on skin includes a housing (12) comprising a long and flat tube of insulating material, a pair of electrodes (16, 14) disposed at one end of the housing, and an electronic circuit (30) for locating and stimulating the sensitive point. One of the electrodes (14) is a central electrode in a shape of an axle surrounded by an insulating zone (18) made of insulating materials. The central electrode (14) is thicker in the direction of radius than the diameter of a sensitive point. The other electrode (16) is an annular electrode surrounding the insulating zone (18) in a coaxial arrangement around central electrode (14).

10 Claims, 6 Drawing Figures

ELECTRO-THERAPEUTIC DEVICE

CROSS-REFERENCE TO RELATED APPLICATIONS

This is a continuation-in-part of U.S. patent application Ser. No. 06/601,167, filed Apr. 17, 1984.

BACKGROUND OF THE INVENTION

1. Field of the Invention

This invention relates to a device for probing and accurately locating a sensitive point on the skin and for giving electric and localized stimulation to the sensitive point by a pair of electrodes, and more particularly, to a device in which a pair of electrodes are closely positioned to each other so that one electrode makes contact with a non-sensitive area extremely near a sensitive point, while the other electrode is precisely aligned in contact with the sensitive point.

2. Description of the Prior Art

It has been long known by experience in Oriental medicine that particular symptoms of illnesses, such as stiff muscles and pains, are reflected at specifically corresponding acupuncture points. Meridians on the body can be treated for relief and/or cure of the symptoms by means of insertion of a needle, moxibustion or adhesion of a tape with a metal grain.

An acupuncture point has been previously located by a skilled therapist or doctor who has accumulated many touch or palpable experiences, or has been approximated by referring to locations shown in a diagram.

It has been recently ascertained that the existing treatment of an acupuncture point is specifically nothing but stimulation of the skin. Such stimulation can also be made electrically with the benefit that skin damage and pain are not caused. It has also recently been ascertained that an acupuncture point is identical with an electrically low resistant sensitive point on the skin. The discovery of the facts mentioned above has led to discoveries of new sensitive points, in addition to the previously known acupuncture points, which are useful for treatment of various symptoms of illnesses, and to the introduction of many electrical devices for locating and stimulating the sensitive point.

U.S. Pat. No. 3,207,151, issued Sept. 21, 1965, to Masao Takagi, entitled "Instrument for Locating Particular Points Caused by Visero-Vascular Reflex", discloses a device for locating and stimulating a sensitive point. The device is constructed such that a cylindrical casing 14 containing electronic circuits has at its top a grip electrode 5 to be held by a patient, a roller electrode 6₁ for conducting low AC current together with a needle-like stimulating electrode 6₂ for conducting high AC current at the other end of the casing, and a switch 8 for selecting the electrode 6₁ or 6₂. Such construction assumes a long electric route of bodily conduct between the electrode 5 and the roller electrode 6₁, that is, the electric path through the body, including meridians, is formed between the skin of the hand holding the grip electrode 5 and a sensitive point contacted by the electrode 6₁ after a scanning exploration. There are, however, many sensitive points on the palms and tips of the fingers, so the device is disadvantageous in that correct contact of the electrode 6₁ with a sensitive point is not truly indicated because a reading of ammeter 12 and the sound tone of speaker 13 may vary depending on whether any sensitive point of the palm and finger tips touches the electrode 5 and on how many sensitive points of the palms and finger tips are in contact with electrode 5.

Because of the above mentioned reasons, it is also very difficult for the needle-like electrode $6_2$ to probe and detect a sensitive point in an area indicated by electrode $6_1$.

The center of a sensitive point (which is about 2–2.5 mm in diameter) and its surrounding area are different in electric resistance, which adds another disadvantage in that it is almost impossible for the needle-like tip of the electrode $6_2$ to correctly contact the true center of the sensitive point as the ammeter cannot measure it.

Another disadvantage of the prior art device is that power is heavily consumed because the electrical resistance of the circuit between the hand and the sensitive point to be stimulated is low and the power of the battery housed in the pen-styled compact cylindrical casing is used up very soon, in less frequent application, making the device impractical for convenient use.

The above described disadvantages of the prior art are not eliminated in similar prior art devices. Their common practices include providing the electronic circuitry in a three-dimensional housing with a pair or more of out-going lead wires, a pair of which is connected to an electrode to be held by the user while the other pair is connected to a needle-like electrode for locating and stimulating the sensitive point. The electronic circuitry is also usually provided with a switch for selection of a locating circuit or a stimulating circuit.

SUMMARY OF THE INVENTION

It is accordingly an object of this invention to provide a device for electrically locating and stimulating a sensitive point by a pair of electrodes disposed in the housing with a small distance between them so that the electrodes are not short-circuited by a sensitive point.

It is another object of this invention to provide a device for locating and confirming the sensitive point by a pair of electrodes, closely disposed to each other, that cooperate together in sliding to probe around the sensitive point, where moisture and skin thickness are almost uniform, without simultaneously contacting two or more sensitive points.

It is a further object of this invention to provide a device for applying stimulation through a pair of electrodes by pressing a selector switch with the forefinger of the hand holding the device so as to activate a stimulator circuit in the electronic circuitry while the pair of electrodes, which are arranged to be close to each other, is held in a position correctly aligned with the detected sensitive point.

It is a still further object of this invention to provide a device that enables positive and precise location of a true sensitive point by indication of a glowing indicator lamp and activation of a buzzer driven by a probing circuit which is activated only when a central electrode is positioned on the center of the sensitive point, making an annular electrode around it conductive because the pair of electrodes is arranged such that one of the pair comprises the central electrode surrounded by an annular electrode equi-distant from the central electrode, forming a coaxial arrangement, and the distance is such that a single sensitive point never contacts both electrodes at the same time.

It is yet another object of this invention to provide a device for handy application at any time and at any place. The device is very portable and compact in size, enabling the device to be carried in the breast pocket of a suit jacket. The device is in the shape of a pen-style compact flat tube, and employs a pair of coaxial formed electrodes requiring no out-going lead wires.

It is still another object of this invention to provide a device to avoid incorrect operation by making the locating and stimulating operations positive and precise, realized by such an arrangement that the pair of slanted electrodes is disposed at one end of the pen-style flat housing which has operating components on its narrow front face, so that manipulation of the switch to select the electronic circuits is done easily and securely by a forefinger when the housing is held and slanted like a writing pen so as to make the electrodes correctly contact the skin.

It is still another object of this invention to provide a device to generate strong stimulation for application at a sensitive point by means of a peaked pulse wave of high potential.

It is still a further object of this invention to provide a device in which the electric charge of the peaked pulses of high potential comes out of the coaxially arranged center electrode in the form of a dense beam to stimulate collectively the sensitive point, so that it is diffused in all directions, forming an arc to return to the annular electrode and passing through the muscle near the sensitive point.

It is still another object of this invention to provide a device that operates for a long period of time on a small power source, such as two 1.5 V batteries, contained in the pen-size housing, owing to its small power consumption, in spite of which the stimulating capacity is equivalent to or exceeds the existing bulky devices and even the stationary type equipment used at clinics because of the stimulation method of the peaked pulse of high electric potential.

When the alignment of the center electrode to the sensitive point is confirmed by the indications, the selector switch can be actuated to close and connect the stimulator circuit where a DC input fed to the high potential pulse generating circuit appears at the center electrode in the form of a perfectly peaked pulse wave with its lower level clipped at a predetermined value in a discriminating circuit. The stimulation lasts as long as the switch is depressed. The output of the high potential, pulse of very weak current from the center electrode passes through the hypodermic sensitive point and its vicinity of electrically high resistance and returns back to the annular electrode. The selector switch is released to finish the stimulation, and the power switch is turned off when all the operation is through.

The device of this invention for the above described objects is provided with an electrode head slanted by 10°–35° against the center line of the housing, of a coaxial arrangement at one end of the housing which is in such a shape that, when held by a user in a manner like holding a pen, it snugly fits in the hand and both the electrodes evenly contact the skin, thus facilitating easy and precise probing and stimulation of the sensitive point. In addition to the above, unexpected dislocation of the set of electrodes is prevented and all the operational manipulations are made precisely because of the disposition of the switches which are made ready once the power switch on top of the housing is pressed and which are arranged on the lengthwise front face opposite the electrodes.

When the power switch is pressed ON, the electrodes in the coaxial arrangement connected in parallel to the locating circuit in the electronic circuitry are automatically activated, energizing the red LED connected to the probing circuit through the comparator. The device is set as described above for probing manipulation and scanning over the skin, and detection of the sensitive point is indicated by the glowing of the green LED. When the red LED is turned off, the piezo sound buzzer, driven by the oscillator, sounds an alarm, resulting from the flow of current between the electrodes when the center electrode is positioned on the sensitive point.

The preferred embodiments of the invention are illustrated in the drawings.

DETAILED DESCRIPTION OF THE PREFERRED EMBODIMENT

Figure 2:
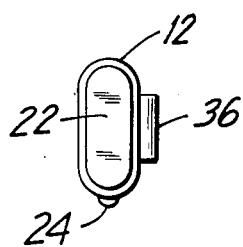
FIG. 2 is a plan of the device shown in the FIG. 1.
Figure 3:
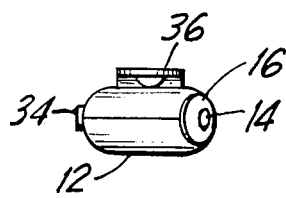
FIG. 3 is a bottom view of the device shown in FIG. 1.
Figure 1:
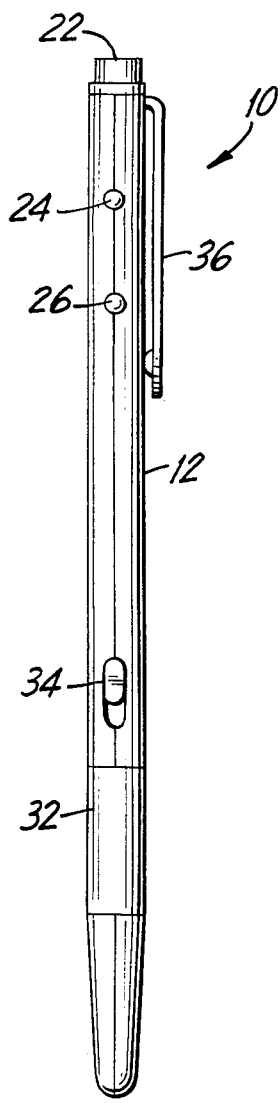
FIG. 1 is a front view of the preferred embodiment of the probing and stimulating device of the present invention.

A preferred embodiment of the present invention of a locating and stimulating device of the sensitive points of the body is shown generally at 10 in FIGS. 1 and 3.

Figure 4:
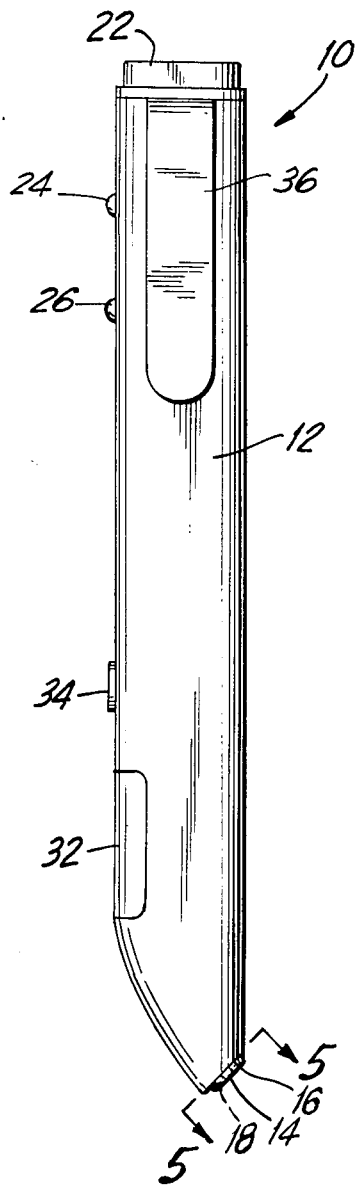
FIG. 4 is a side view of the device shown in FIG. 1.
Figure 5:
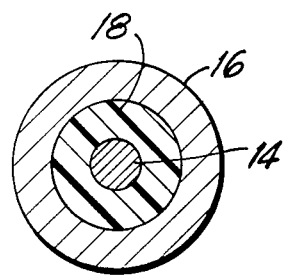
FIG. 5 is an enlarged sectional view along the line 5—5 in FIG. 4 illustrating the coaxial arrangement in which the center electrode is surrounded by the annular electrode with equi-distance spacing.

A housing 12 comprising device 10 is, as shown in FIG. 1 or FIG. 4, pencil-shaped in terms of shape and size and has an elliptical cross-section to form a flattened tube. Housing 12 is normally mold-injected from synthetic resin, but can be formed from light alloy metal with a coating of electrically insulating materials on all the surfaces.

A center axle electrode 14 and an annular electrode 16 with an insulating material 18 between them forming a coaxial arrangement are disposed at the bottom of housings 12 and toward the rear thereof. An angle is made between the center line of electrodes 14 and 16 and that of housing 12.

Figure 6:
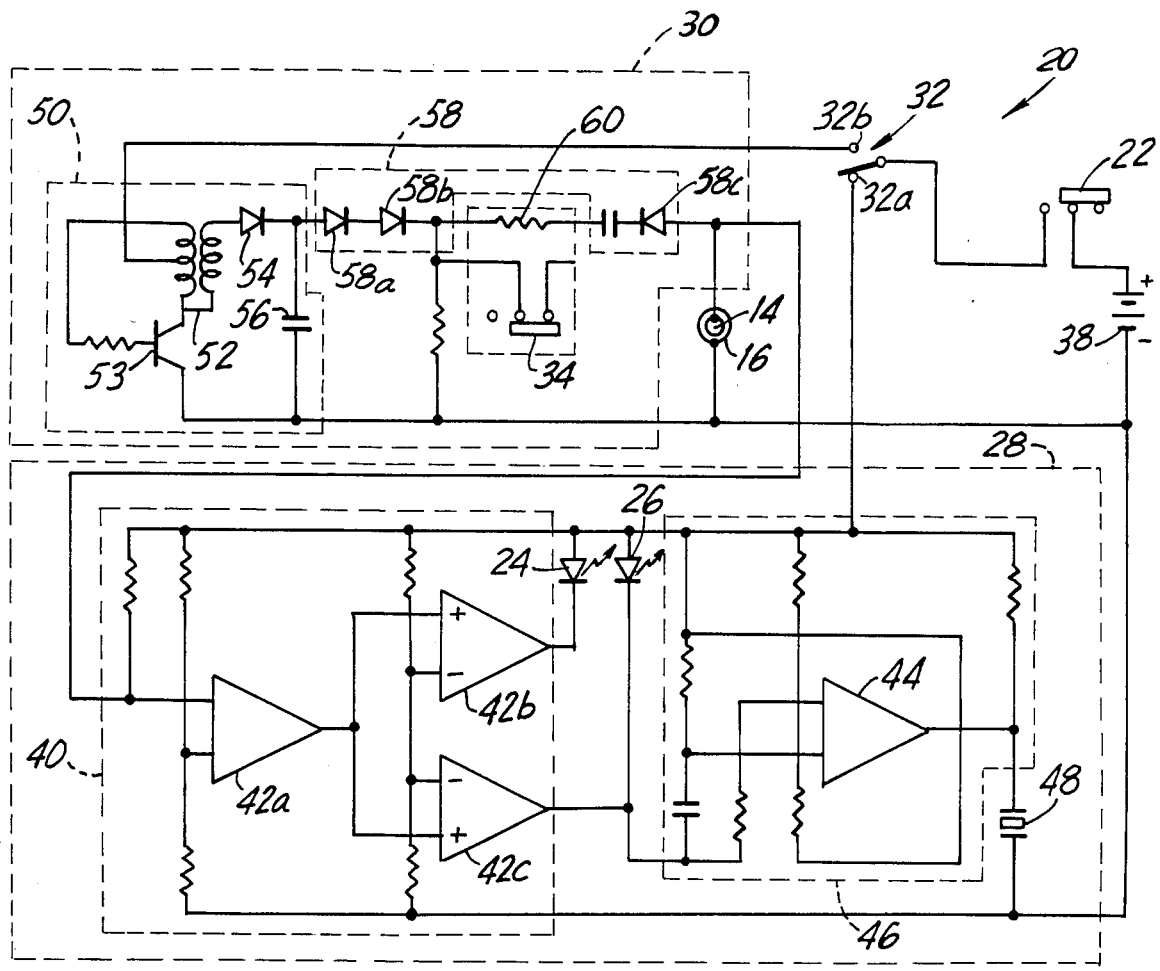
FIG. 6 is a diagram of a preferred embodiment illustrating the electronic circuitry showing the principle of operation of the present invention.

Electronic circuitry 20, which is connected to electrodes 14 and 16 as shown in FIG. 6, is contained in housing 12, on the top of which a push-button power switch 22 is mounted. Indicators and selector switches are arranged on the narrow lengthwise front surface; a red LED 24 on the top is a power pilot lamp to indicate power ON, and therebelow is an LED 26 as a sensitive point detection lamp to indicate contact between the central electrode and the sensitive point. Apart from the indicator, but near the bottom of the housing, a slide switch 34 is provided for selecting high and low output stimulating potential. Near the extreme bottom a push-button selector switch 32 is provided that is pressed when the green LED 26 glows, and turns on stimulator circuit 30, disconnecting circuit 28 in circuitry 20 (shown in FIG. 6) while depressed.

The device of this invention in the shape and with arrangement of the operating components as mentioned above is compact and portable, like a pencil. It does not become bulky in carrying because of the flat shape of the housing.

When housing 12 is held slanted like a pencil, electrodes 14, 16 make a perfect and proper contact with the skin, and the flatness of housing 12 assures holding and positioning stability that avoids unexpected rotation in the hand, thus preventing sliding of the electrodes 14, 16 off the point or poor contact of either electrode with the skin. As device 10 is thus held, its handling is very much like writing letters or drawing designs so that a comfortable holding manner helps precise scanning for the sensitive points, eliminating off-positioning and providing long lasting stimulating operation. Furthermore, switches 32 and 34 are positioned within easy reach of the forefinger when housing 12 is held properly for application, so that both switches 32, 34 are operated securely and correctly by a finger tip holding the electrode 14 in correct contact with the sensitive point.

The tips of electrodes 14 and 16 are a little raised from the surface of the in-between insulating material 18 which, therefore, does not contact the skin. Thus, the surface of insulating material is prevented from becoming a bypassing conduit between electrodes 14, 16 by getting wet from moistened skin. Therefore, the recess of the surface of insulating material 18 saves power and helps form an electric path from the part of the skin contacted by one electrode through the hypodermic muscle to the part of the skin contacted by the other electrode.

The width of the annular insulating zone made from insulating material 18 is larger than the diameter of a sensitive point, so that both electrodes 14, 16 are never bridged by it. Detection of the sensitive point center is made impossible and stimulating effect is greatly reduced if electrodes 14, 16 are closed through a sensitive point, because more electric current flows through the sensitive point than when central electrode 14 is in contact with the center of the sensitive points, thus activating green LED 26 and the buzzer. The diameter of a sensitive point is known to be about 2 mm, and the width of the insulating zone of the preferred embodiment is 2.5–3 mm, which is the nearest possible positioning distance between electrodes 14, 16 for the maximum stimulating effect when collective electric energy is loaded between the hypodermic sensitive point and its immediately surrounding portion of non-sensitive area (where the electrical resistance is high).

Electronic circuitry 20 of a preferred embodiment of this invention will now be described by way of example with reference to FIG. 6.

A locating circuit 28 enclosed in a dotted line and electrodes 14 and 16 are connected in parallel to a power source battery 38 through a power switch 22. Two 1.5 V batteries are used in this preferred embodiment.

The power switch 22 is connected in series to a selector switch 32, a contact 32a of which is normally closed and a contact 32b normally open. Pressing selector switch 32 opens the contact 32a, while it is depressed, removing the locating circuit 28 from the power source. At the same time, the contact 32b is closed, activating a stimulator circuit 30. Stimulator circuit 30 is connected in parallel to electrodes 14 and 16.

When power switch 22 is turned on for exploration of the sensitive point, electrodes 14 and 16 are energized by battery 38 through normally closed contact 32a and, at the same time, the power is fed to a pre amplifier 42a of a converter 40 in the locating circuit, which drives a gate amplifier No. 1 42b to activate red LED 24, power pilot lamp, when electrodes 14, 16 contact the electrically low resistant skin near the sensitive point. In scanning, the electrodes slide on the skin for exploration of a sensitive point. Red LED 24 is kept turned on even when annular insulating material 18 reaches the sensitive point after annular electrode 16 contacts the sensitive point. When the scan brings center electrode 14 to the exact center of the sensitive point on the skin, the low electrical resistance of the sensitive point increases the output current of electrode 14, with the resulting activation of a gate amplifier No. 2 42c which turns on green LED 26, the sensitive point detecting lamp, while in turn the gate amplifier No. 1 42b is cut off, turning off red LED 24. At the same time, an oscillator 46 (shown in a dotted line), incorporated with amplifier 44, is energized to activate a piezo-sound buzzer that sounds an alarm.

The above-described activations of green LED 26 and the buzzer is a confirmation that center electrode 14 is correctly aligned on the center of the sensitive point and that selector switch 32 is ready to be pressed so as to activate stimulator circuit 30 by closing normally open contact 32b. Once ready selector switch 32 as described above is pressed, both green LED 26 and buzzer 48 are turned off.

When selector switch 32 is pressed, energy of power source battery 38 is fed to a high voltage pulse generator circuit 50 in stimulator circuit 30. Input voltage applied to the primary of a differential transformer 52 of circuit 50 appears as a peaked pulse of high potential incorporated with a transistor 53 and a capacitor 56. The output pulse of pulse generating circuit 50 has its lower voltage portion below a pre-determined value clipped at a discriminating circuit 58 consisting of diodes 58a, 58b and a zener diode 58c. Only the purely peaked wave portion of the pulse is sent out to electrode 14. Meanwhile, high or low selection of the output Pulse voltage, selected by a slide switch 34, is connected across a resistor 60 in the above-described discriminating circuit 58.

The output of the high potential pulse of very weak current from electrode 14 passes through the hypodermic sensitive point and its vicinity of electrically high resistance and returns back to electrode 16. Therefore, the stimulation is positively localized, as none of the supplied electricity is diffused to unnecessary parts of the body and no unknown path of electricity is made through the body, which requires weak current for effective stimulation, resulting in a saving of electric power. Although the current is weak, the sensitive point is strongly stimulated because of the peaked pulse of high potential. Also, the stimulation is powerful, as the output electric charge passes through the sensitive point in a dense beam. The return trip of the electric charge is such that the beam discharged directly forward is radiated to all the directions, curving in an arc through the muscle and the part of skin and is collected by electrode 16.

As described above, the device of this invention is neatly and compactly housed, realizing handy manipulation held by a user with consequential correctness in locating and stimulating the sensitive point. Its battery is of a small capacity and is restricted by the compactness of the housing and lasts long owing to the small power consumption of the device In spite of the small size of the device, the stimulating strength is equivalent to or exceeds the existing large size portable devices and the stationary type equipment used in clinics because of the sensitive point stimulating method by the aforementioned high potential pulse wave.

The device of this invention is also beneficial and truly effective as the precise detection of the sensitive point is correctly indicated by both the glow of green LED 26 and the alarm sound of buzzer 48, which are activated only when center electrode 14 is aligned with the center of the sensitive point. Electrodes 14 and 16 of the coaxial arrangement are not made conductive when annular electrode 16 or insulating material 18 makes contact with the sensitive point, or even when center electrode 14 is in contact with the circumferential area of the sensitive point, in which no indication is made. When green LED 26 comes on, the red power LED 24 is turned off.

We claim:

1. A probing and stimulating device for use with a sensitive point on the skin comprising:

a housing comprising a long and flat tube of insulating material;

a pair of electrodes disposed coaxially at one end of said housing, one of said electrodes forming a first center electrode having an axle shape surrounded by an insulating zone made from insulating materials, said insulating zone being thicker in the direction of radius than the diameter of a skin sensitive point, and the other of said electrodes forming a second annular electrode immediately surrounding the insulating zone in a coaxial arrangement with respect to said first center electrode;

electronic circuit means for locating and stimulating the sensitive point, said electronic circuit means including a locating circuit for locating a skin sensitive point, a stimulator circuit for stimulating the skin sensitive point, and a selector switch having a first position for selecting operation of the locating circuit and a second position for selecting operation of the stimulating circuit, said locating circuit having a first lead for connecting the locating circuit to the selector switch, a second lead for connecting the locating switch to the first center electrode, and a third lead for connecting the locating circuit to the second annular electrode and to an electrical ground, said stimulating circuit having a first lead for connecting the stimulating circuit to the selector switch, a second lead for connecting the stimulating circuit to the first center electrode and a third lead for connecting the stimulating circuit to the second annular electrode and to an electrical ground, said locating circuit comprising a first lamp for indicating when the locating circuit is selected, whether the pair of electrodes are in contact with electrically low resistant skin, a second lamp for indicating, when the locating circuit is selected, alignment of the pair of electrodes with a skin sensitive point, a converter circuit connected to said second and third leads of the locating circuit and connected to said first lead through said first lamp and connected again to said first lead through said second lamp, said converter circuit comprising a first comparator for driving the first lamp when the electrodes are in contact with electrically low resistant skin, a second comparator driving the second lamp when the resistance across the electrodes drops, thereby indicating alignment with a skin sensitive point, said stimulating circuit comprising an electrically high potential pulse generator for developing a high potential peaked pulse, and a discriminating circuit for cutting off the lower level of said peaked pulse below a predetermined value, thus generating a pulse with a peaked crown of high potential for supplying to said electrodes.

2. The probing and stimulating device of the sensitive point according to claim 1, wherein said coaxial electrodes are disposed at one end of said housing, have a slanted arrangement, and have a center line that meets at an angle with a center line of said housing, and wherein said housing has a flat elliptical sectional shape.

3. The probing and stimulating device of the sensitive point according to claim 2, wherein said power switch is disposed on the top of said housing; and wherein said power first lamp, and said second lamp are arranged on a narrow lengthwise front face of said housing.

4. The probing and stimulating device of the sensitive point according to claim 3, wherein said selector switch is depressable 5. The probing and stimulating device of the sensitive point according to claim 1, and further comprising:
   second
   a piezo sound buzzer connected in parallel to said detecting indication lamp via oscillator circuit activated simultaneously with said detecting indication lamp.

6. The probing and stimulating device of the sensitive point according to claim 1; further comprising a power source of two 1.5V batteries.

7. The probing and stimulating device of the sensitive point according to claim 1; wherein said stimulating circuit further comprises the discriminating circuit of two diodes and one zener diode connected in series.

8. The probing and stimulating device of claim 7 further comprising a slide selector switch and wherein said discriminating circuit further comprises a resistor connected between said zener diode and one of said two diodes, wherein said slide selector switch is connected across said resistor for selecting between a first path in which the resistor between said zener diode and one of said two diodes is bypassed and a second path in which said resistor is not bypassed, said second path thereby being of a higher resistance to cause the peaked pulse to have relatively lower voltage than the peaked pulse resulting when the first path is selected.

9. The probing and stimulating device of the sensitive point according to claim 8; wherein said slide selector switch is disposed in a narrow lengthwise front face of said housing.

10. The probing and stimulating device of claim 1 wherein said peaked pulse generator of high electric potential comprises a transistor, a differential transformer having a primary winding which receives a direct current imput and a secondary winding which in combination with the transistor differentiates the direct current wherein one end of the primary winding is connected to the base of the transistor and the other end of the primary winding and one end of the secondary winding are connected to the connector of the transistor, a diode which receives the output current from the secondary winding, and a capacitor for switching the output current as it passes through the diode to produce a peaked pulse of high potential and weak current.

* * * * *